US005863498A

United States Patent [19]

Houston

[11] Patent Number: 5,863,498

[45] Date of Patent: Jan. 26, 1999

[54] DECONTAMINATION APPARATUS DOOR UNIT

[75] Inventor: John C. Houston, Erie, Pa.

[73] Assignee: Steris Corporation, Mentor, Ohio

[21] Appl. No.: 797,601

[22] Filed: Feb. 7, 1997

[51] Int. Cl.[6] .................... A61L 2/00; A61L 9/00

[52] U.S. Cl. .................... 422/28; 16/78; 16/223; 16/374; 422/1; 422/3; 422/105; 422/292

[58] Field of Search .................... 422/292, 300, 422/117, 119, 105, 1, 28, 3; 16/223, 374, 78

[56] References Cited

U.S. PATENT DOCUMENTS

| | | | |
|---|---|---|---|
| 4,431,015 | 2/1984 | Noren | 134/55 |
| 4,607,760 | 8/1986 | Roche | 220/314 |
| 4,731,222 | 3/1988 | Kralovic et al. | 422/37 |
| 4,797,254 | 1/1989 | Seidel | 422/49 |
| 5,037,623 | 8/1991 | Schneider et al. | 422/292 |
| 5,391,360 | 2/1995 | Kochte et al. | 422/292 |

*Primary Examiner*—Krisanne Thornton
*Attorney, Agent, or Firm*—Fay, Sharpe, Beall, Fagan, Minnich & McKee

[57] ABSTRACT

A decontamination device (10) including a housing (12) and a chamber (16) for receiving articles to be decontaminated by at least one of washing, disinfecting and sterilizing. A control pad (20) for an operator to input control instructions for controlling decontamination cycles to which the articles are subjected. The control pad being disposed adjacent an exterior of the housing and being accessible to the operator through an opening (24) in the housing (12). A door (30) covering the opening (24) and being hingedly attached to the decontamination device by a mechanism (26) disposed entirely within the housing when the door is in a closed position. The mechanism (26) can be a leaf spring (36) having a first end connected with a pivot pin (42) to the door (30) and a second end secured to an internal region (40) of the housing (12). During opening and closing of the door, the lower edge (48) of the door, in cooperation with the outer panel of housing (12), provides a cam type action which causes bending of the leaf spring (36) and allows travel of a longitudinal axis of the pivot pin (42) outwardly and inwardly relative to the housing (12) as the door (30) is opened and closed respectively, and allows about 180° of rotation of the door between open and closed positions. The door can include a horizontal slot (34) through which a paper tape (32) of a printer (22) is fed.

17 Claims, 4 Drawing Sheets

26
24
46
44
36
42
48
34
30
38
12
40

26
38
36
40
24
48
46
42
44
34
30
12

26
38
36
40
48
44
24
46
42
34
30
12

26
36
38
42
46
40
30
34
44
48
12

DECONTAMINATION APPARATUS DOOR UNIT

BACKGROUND OF THE INVENTION

The present invention relates generally to the decontamination art. It finds particular application in the sterilizing and disinfecting apparatus typically employed with medical, dental, veterinary, mortuary, and laboratory instruments and equipment and will be described with particular reference thereto. It will be appreciated, however, that the invention may be applicable to a wide variety of apparatus used in sanitary environments.

Medical, dental, surgical, veterinary, and laboratory equipment and instruments are often sterilized by steam and/or reagent treatments. More particularly, an apparatus is provided which isolates the equipment and instruments in these respective environments for a sufficient period of time to complete decontamination. The steam autoclave devices of the type described in U.S. Pat. Nos. 4,193,818; 4,226,642; and 4,601,300 and the reagent sterilization devices as described in U.S. Pat. Nos. 4,731,222; 5,037,623; and 5,391,360 represent decontamination apparatus with which the present invention is particularly suited. Each of these patents is herein incorporated by reference.

Often, decontamination apparatus are provided with a primary, frequently used control panel and a secondary, infrequently used control panel, each allowing an operator to input information to a microprocessor based control. In addition, decontamination apparatus often include a paper printout of sterilization parameters to allow a permanent record or receipt for each sterilization procedure to be printed. To provide easy access to the control panels, a printer paper roll and the printer itself, these elements are located on the exterior of the decontamination apparatus. Although the primary control panel is often left exposed for easy access, the other elements are preferably covered by a door to prevent unintentional contact and/or damage.

Historically, a conventional hinge has been used to allow the door to be manually opened. To allow the door to open adequately, the hinge has been positioned on an outer wall of the decontamination apparatus. Moreover, to obtain 180° of rotation of the door, the pivot axis provided by the hinge was outside the plane of the apparatus' outer wall. This is aesthetically undesirable and has often led to the use of small, less visible hinges that possess an inherently low strength. Furthermore, these exposed hinges and their attachments are prone to being damaged and have proven difficult to clean because most surfaces of the hinge are not readily accessible.

The present invention contemplates a new and improved door assembly which overcomes the above-referenced problems and others.

SUMMARY OF THE INVENTION

In accordance with one aspect of the present invention, a decontamination device having a chamber for receiving articles to be decontaminated by either washing, disinfecting or sterilizing is provided. A control pad is also provided to allow an operator to input instructions to control decontamination cycles within the chamber. The chamber is contained within a housing and the control pad is positioned adjacent the exterior of the housing and is accessible to the operator through an opening in the housing. A door assembly covers the opening which exposes the control pad. The door assembly is hingedly connected to the decontamination device by a moveable member disposed entirely within the housing when the door is closed.

In accordance with a more limited aspect of the invention, the moveable member is either a resilient element allowing the pivot connection to flex or bend outwardly from the walls of the decontamination device or the moveable member is itself pivotally connected to the interior of the decontamination device.

In accordance with another aspect of the invention, the moveable member is sufficiently outwardly extendible from the decontamination device to permit displacement of the pivot access outwardly from the exterior wall of the decontamination unit to allow about 90° of rotation, and preferably, 180° of rotation of the door.

In a more limited aspect of the invention, the door opens vertically and includes top and bottom portions with the pivot connection being located adjacent the bottom of the door. A lower edge of the door extends below the pivot connection and abuts the outer wall of the decontamination unit during opening and closing of the door, creating a camming type action. This camming type action in combination with the inward pull of the resilient member results in a bias on the door that selectively maintains both open and closed positions.

In an even more limited aspect of the invention, the resilient element forming a component of the hinge assembly can act simultaneous as the paper roll retainer for the paper feed mechanism.

One advantage of the present invention is that the door and hinge covering the control panel does not create a significant discontinuity on the outer surface of the decontamination unit. Accordingly, cleaning of the unit is accommodated by the present design.

Another advantage of the present invention is that the hinge assembly for the door is positioned internally to the decontamination unit and the likelihood of damage during handling of the unit is significantly reduced.

Still further advantages of the present invention will become apparent to those of ordinary skill in the art upon reading and understanding the following detailed description of the invention.

BRIEF DESCRIPTION OF THE DRAWINGS

The invention may take form in various components and arrangements of components, and in various steps and arrangements of steps. The drawings are only for purposes of illustrating a preferred embodiment and are not to be considered as limiting the invention.

DETAILED DESCRIPTION OF THE INVENTION

As part of a decontamination unit control user interface, a manually operated door is provided on an outer panel of the decontamination unit to cover and provide access to certain features. More particularly, a control pad for reprogramming of basic operating functions, a printer, and a printer paper roll are those elements of the unit most typically made accessible through a hole in the sterilizer panel and covered by the door.

Figure 2:
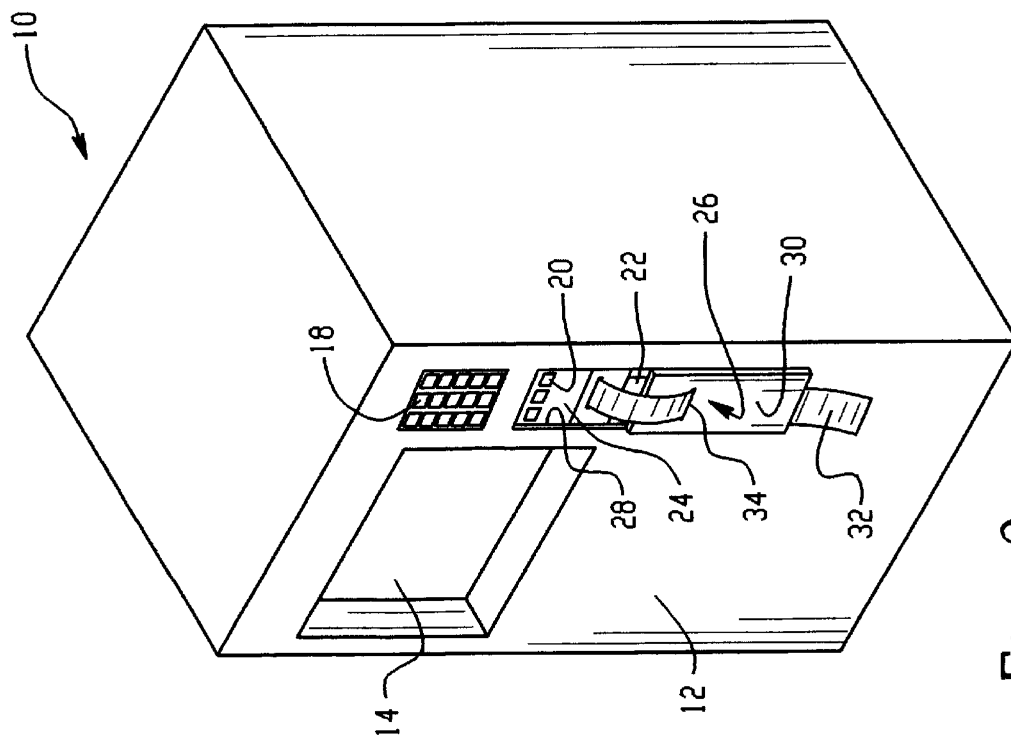
FIG. 2 is a perspective view of the assembly of FIG. 1 with the door in an open position.
Figure 1:
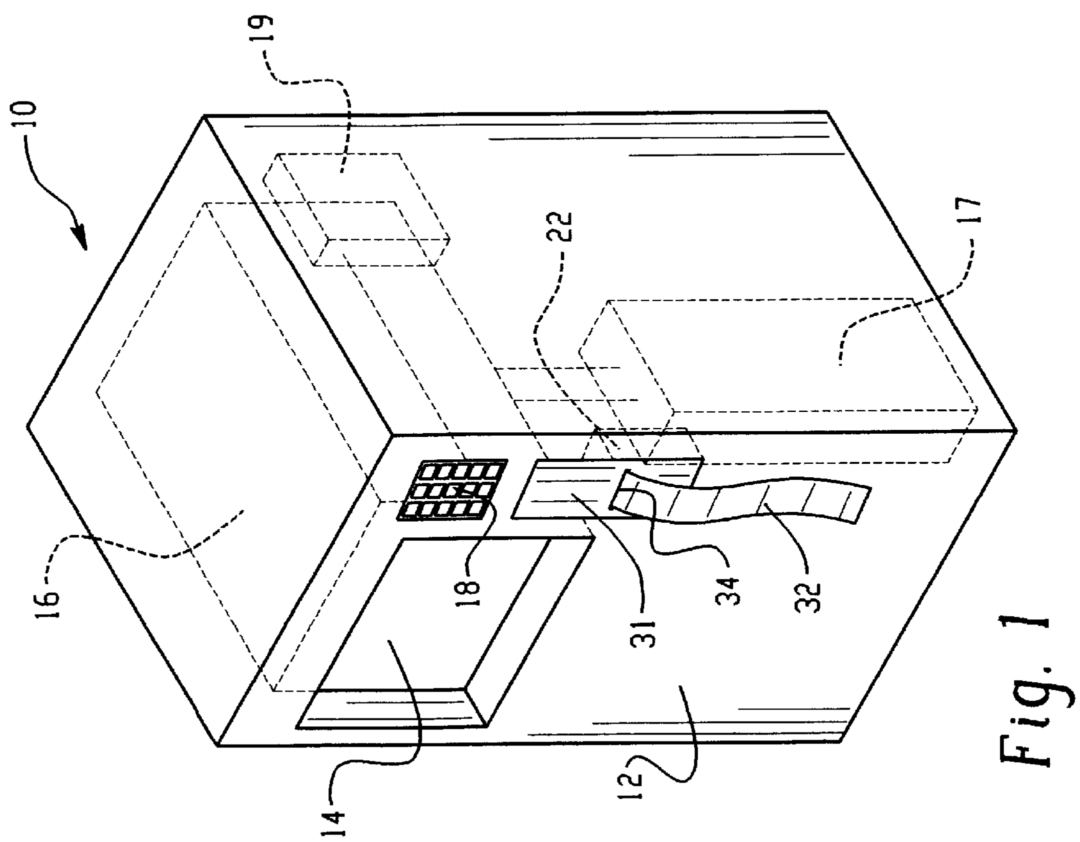
FIG. 1 is a perspective view of a steam autoclave sterilization device with a door in a closed position covering controls and a paper feed assembly.
Figure 4:
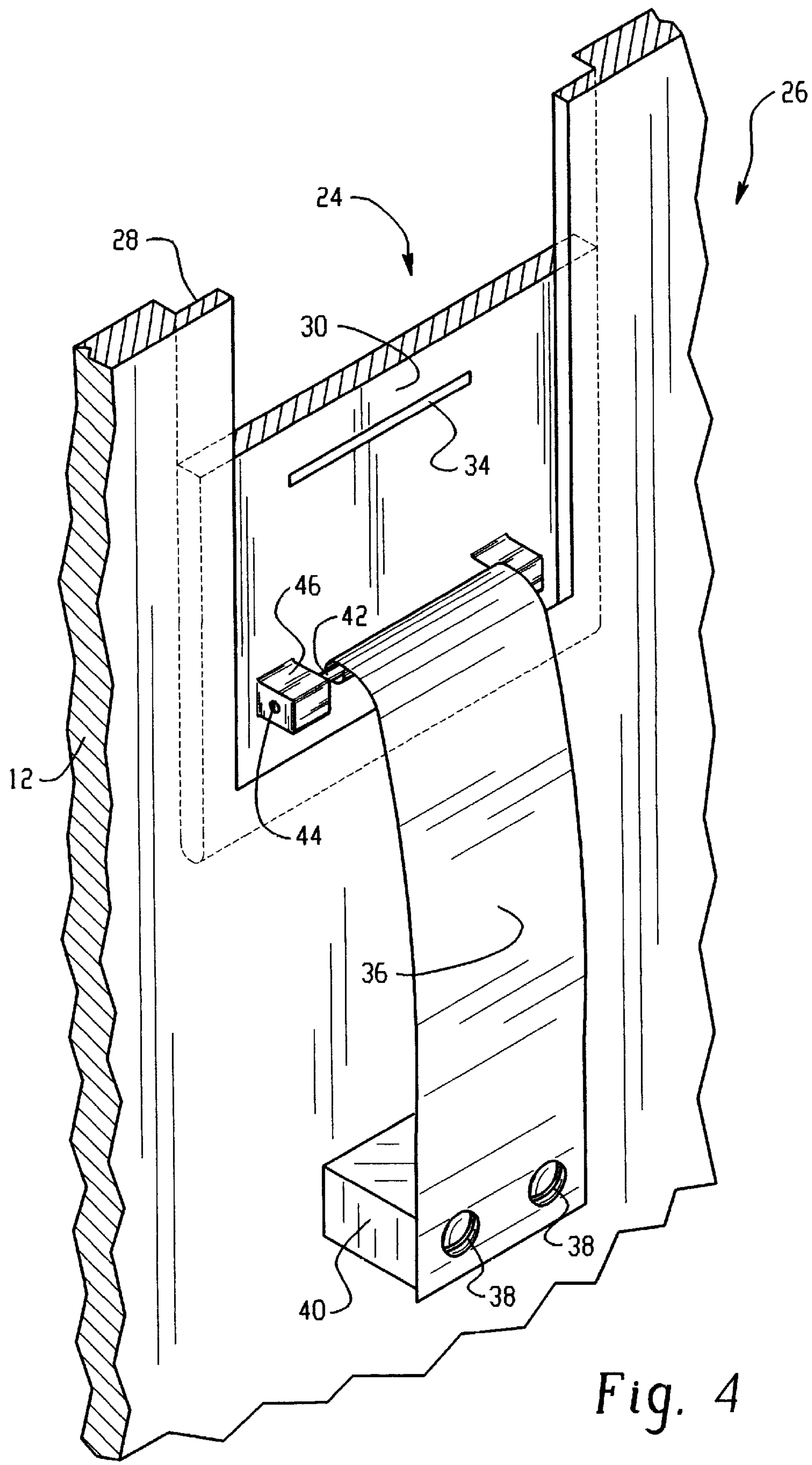
FIG. 4 is a view of the door assembly of FIG. 1 taken from internal of the autoclave.

With reference now to FIGS. 1, 2 and 4, steam autoclave 10 is shown having a front paneled outer wall 12. The front wall 12 includes a port 14 to a sterilization chamber 16, shown in outline, which receives steam from a steam generator 17, also shown in outline. Commonly used control features are accessible via a primary control panel 18 which is in connection with a microprocessor control 19, shown in outline.

In addition, a secondary control panel 20 and a printer 22 are accessible through an opening 24 in the panel 12 covered by a door assembly 26. Optionally, the panel has a recess 28 of about the same size as a door 30 and a depth of about the same thickness as the door. This allows an outerwall 31 of the door 30 to be flush with an outer surface of panel 12. In this embodiment, a finger hole (not shown) may be provided to facilitate opening of the door.

Paper strip 32 is fed through a horizontal slot 34 in door 30. The door 30 opens vertically to accommodate opening of the door without the significant interference with the vertical feed direction of the paper strip. Moreover, with the vertical door opening arrangement the paper slides unencumbered through the horizontal slot 34 throughout the opening and closing of the door 30.

Figure 3C:
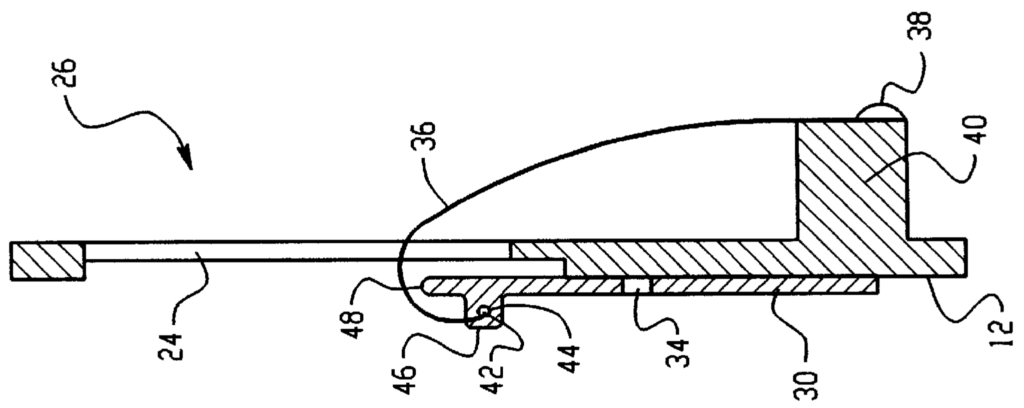
FIGS. 3A, 3B and 3C are side elevation views of the door assembly of FIGS. 1 and 2 in closed, partially open and open positions respectively.
Figure 3B:
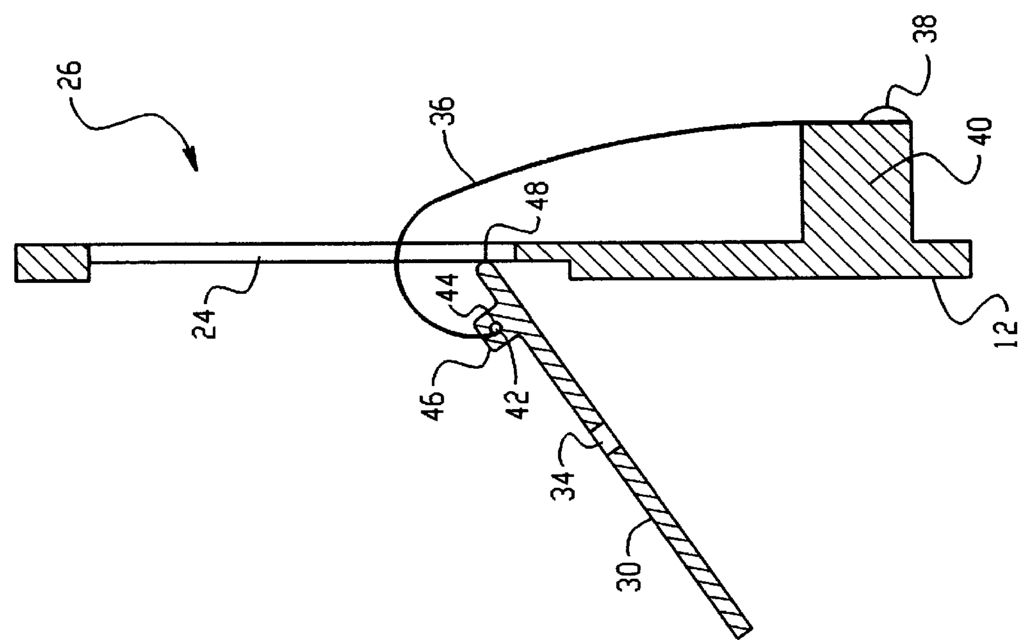
Figure 3A:
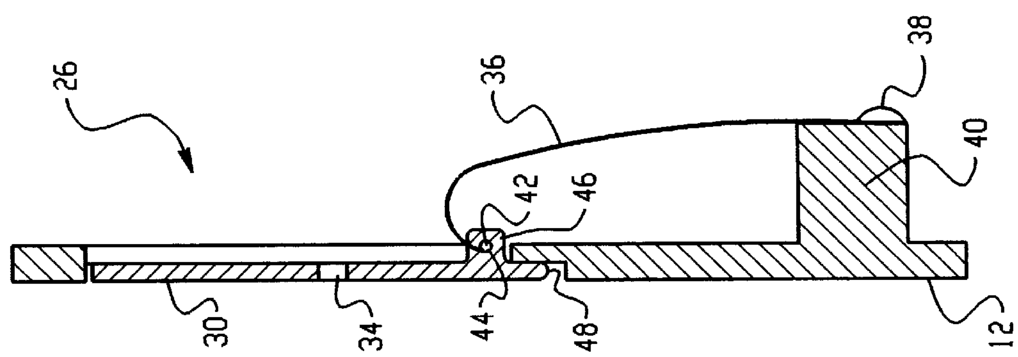

With specific reference to FIGS. 3A, 3B and 3C, the operation of the door assembly 26 is more clearly depicted. Particularly, a leaf spring 36 is secured by a pair of screws 38 (or another type of fastener) to a molded in block 40 on the internal surface of the panel 12. At an opposed end, the leaf spring 36 is attached to a pivot pin 42 received at each end in apertures 44 in keepers 46 integrally molded to the door 30.

As progressively depicted in FIGS. 3A, 3B and 3C, the articulating nature of the pivot axis of the door assembly 26 relative to the panel 12 occurs when the door 30 is manually opened. A lower edge 48 of the door 30 engages the front panel 12 defining one pivot axis, forcing the pivot axis of the pivot pin 42 to move outward. The outward movement is permitted by the resilient nature of the deflecting leaf spring 36.

The flexible nature of the leaf spring allows for articulation of the pivot point. Clearly, the arc of the J in the leaf spring must be large enough to permit full rotation at the bottom edge of the door about the pivot axis. Accordingly, the cam action of the lower door edge causes a "over center" action which essentially snaps the door into both open and closed positions.

In a closed position, the force on the door is inward and maintains the door in a closed position. In addition, the inward force on the door when open, maintains it in an open position. Accordingly, the articulating nature of the pivot axis accommodates maintaining the door both, and selectively, in open and closed positions, yet 180° of rotation is permitted via the depicted hinge apparatus.

Figure 5B:
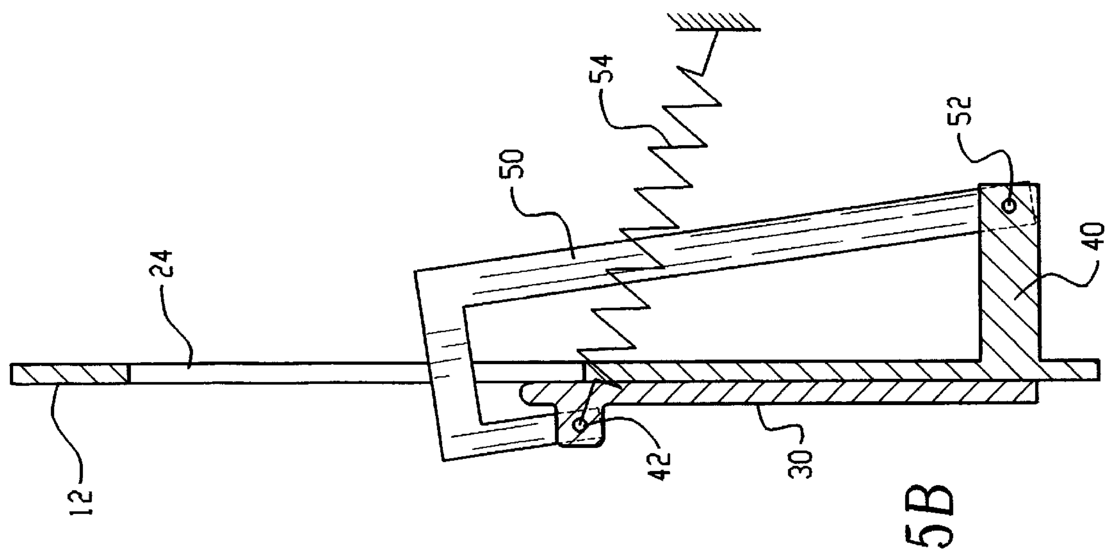
FIGS. 5A and 5B are side elevation views of an alternative door assembly in closed and open positions respectively.
Figure 5A:
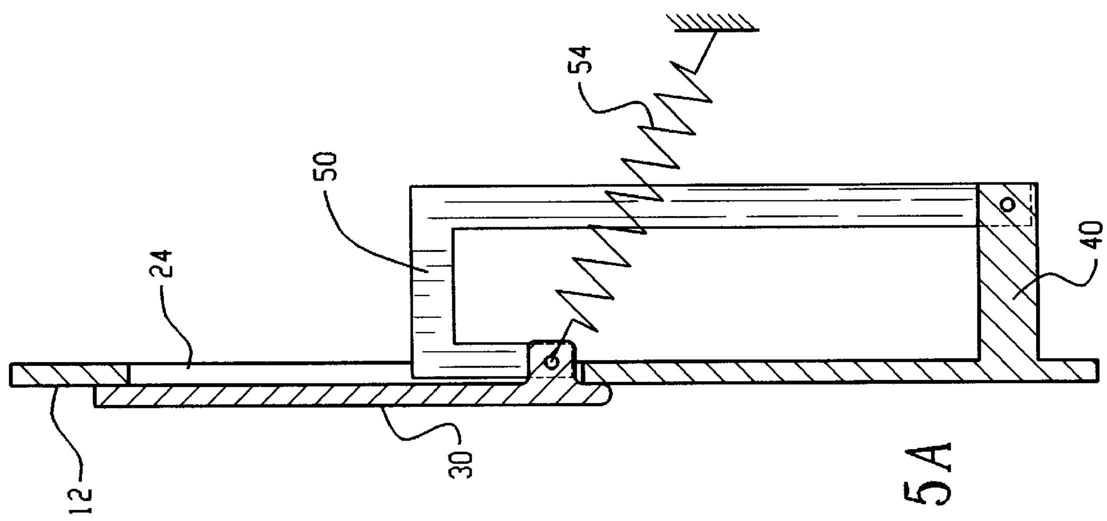

Referring now to FIGS. 5A and 5B, a mechanically divergent, yet functionally similar alternative embodiment of the invention is depicted, wherein a rigid elbow member 50 is interconnected between the pivot pin 42 and a pivot connection 52 with the block 40 on the inner surface of panel 12. In addition, a spring 54 is connected between door 30 and a structure internal to the panel 12. As is clear from the drawings, the manual manipulation of the door again results in articulation of the pivot axis outward from the sterilization unit to allow 180° of rotation of the door. In addition, the spring 54 provides a bias that keeps the door in closed and open positions, respectively. In this embodiment, the door is not recessed within the outer panel of the housing. Of course, whether or not the door is recessed is a design decision, not a prerequisite to functionality of the invention.

The invention has been described with reference to the preferred embodiment. Obviously, modifications and alterations will occur to others upon a reading and understanding the preceding detailed description. It is intended that the invention be constructed as including all such modifications and alterations insofar as they come within the scope of the appended claims or the equivalents thereof.

Having thus described the preferred embodiment, the invention is now claimed to be:

1. A decontamination device including a housing, a chamber in said housing for receiving articles to be decontaminated by at least one of washing, disinfecting and sterilizing, a control pad for an operator to input control instructions which control decontamination cycles that the articles are subjected to, the control pad being disposed adjacent an exterior of said housing and being accessible to the operator through an opening in said housing, and a door covering said opening, said door being attached to a biasing mechanism, said biasing mechanism including a first end secured to an interior of said housing and a second end having a hinge connection to said door, wherein said door includes a lower edge extending below the hinge connection such that downward rotation of a top edge of said door results in the lower edge of the door engaging the housing and acting to cam the hinge connection outward and distend a flexible spring member to bias the pivot connection toward the housing, said biasing mechanism being disposed entirely within said housing when said door is in a closed position and said door having no other hinge connections to said housing.

2. The decontamination device of claim 1 wherein said door is mounted flush with an external surface of said housing in a closed position.

3. The decontamination device of claim 2 wherein said flexible spring member includes a leaf spring.

4. The decontamination device of claim 1 wherein said biasing mechanism includes a rigid L-shaped arm pivotally connected to an internal portion of said housing.

5. The decontamination device of claim 1 wherein the door includes:

a horizontal slot through which a paper tape from a printer is fed;

a horizontal lower edge which rotatably and slidably engages an outer face of the housing such that the door is generally pivotally movable therearound.

6. The decontamination device of claim 5 further including:

a spring connected to the biasing mechanism for biasing the door toward the housing in a closed position and when the door is rotated 180° about a lower edge to an open position.

7. The decontamination device of claim 2 wherein the biasing mechanism includes:

a J-shaped leaf spring that is pivotally connected at one end to the door and fixedly connected adjacent an opposed end to the housing.

8. An apparatus for cleaning, disinfecting or sterilizing comprising:

an outer housing which has an opening for receiving items to be cleaned, disinfected or sterilized and a port;

a door covering the port, said door having a horizontally disposed pivot pin on a lower portion of an interior surface thereof and a lower edge extending below said pivot pin and engaging an outer wall of said housing;

a leaf spring having a first end connected with the pivot pin and a second end secured to an internal region of said housing, such that said lower edge engages said outer wall of said housing and during opening and closing of said door provides a cam action which causes bending of said leaf spring and allows travel of a longitudinal axis of said pivot pin outwardly and inwardly relative to the housing as the door is opened and closed respectively, and allows about 180° of rotation of said door between open and closed positions.

9. A decontamination device for washing, disinfecting or sterilizing having a housing containing at least one of a control panel or a printer covered by a door, the invention further comprising:

the door having as an only attachment to said device a hinged connection to a moveable member secured to an interior surface of said housing, said moveable member allowing travel of at least said hinged connection to said door to facilitate about 180° of rotation around said hinged connection wherein a bottom edge of said door abuts said housing and provides a camming motion during opening and closing of said door.

10. The decontamination device of claim 9 wherein said moveable member includes at least one flexible portion.

11. The decontamination device of claim 9 wherein said moveable member further includes a pivot connection to said housing.

12. The decontamination device of claim 9 wherein said hinged connection is disposed internally of said housing when said door is in a closed position.

13. The decontamination device of claim 12 wherein said hinged connection is disposed externally of said housing when said door is in an open position.

14. The decontamination device of claim 9 including a slot to accommodate a paper feed in said door.

15. The decontamination device of claim 9 wherein said travel is sufficient to facilitate at least about 180° of rotation around said pivot connection.

16. The decontamination device of claim 9 wherein said door includes a top and bottom portion and said pivot connection is located adjacent said bottom portion.

17. A method of decontaminating articles by at least one of washing, disinfecting and sterilizing comprising:

providing a chamber for receiving the articles to be decontaminated;

providing a housing around said chamber which has an opening for positioning the articles in the chamber; providing at least one of a control panel or a printer adjacent said housing and accessible to an operator through a port in said housing;

providing a door covering the port, said door having a horizontally disposed pivot pin on a lower portion of an interior surface and a lower edge extending below said pivot pin and engaging an outer wall of said housing, a leaf spring having a first end connected with the pivot pin and a second end secured to an internal region of said housing during opening and closing of said door, such that said lower edge provides a cam action which causes bending of said leaf spring and allows travel of a longitudinal axis of said pivot pin outwardly and inwardly relative to the housing as the door is opened and closed respectively, and allows about 180° of rotation of said door between open and closed positions; and placing the articles in said chamber and decontaminating the articles and selectively, and periodically, controlling or monitoring said decontaminating by opening said door to adjust said control panel or service said printer.

* * * * *